United States Patent [19]
Lipp et al.

[11] Patent Number: 5,858,394
[45] Date of Patent: Jan. 12, 1999

[54] AGENT FOR TRANSDERMAL ADMINISTRATION THAT CONTAINS GESTODENE ESTERS

[75] Inventors: Ralph Lipp; Henry Laurent; Clemens Günther; Jutta Riedl; Peter Esperling; Ulrich Taüber, all of Berlin, Germany

[73] Assignee: Schering Aktiengesellschaft, Germany

[21] Appl. No.: 602,808
[22] PCT Filed: Jul. 24, 1994
[86] PCT No.: PCT/EP94/02496
§ 371 Date: May 21, 1996
§ 102(e) Date: May 21, 1996
[87] PCT Pub. No.: WO95/05827
PCT Pub. Date: Mar. 2, 1995

[30] Foreign Application Priority Data

Aug. 26, 1993 [DE] Germany .......................... 43 29 242.9

[51] Int. Cl.$^6$ ................................ A61F 13/00; A61K 9/70
[52] U.S. Cl. ............................................ 424/449; 424/448
[58] Field of Search ..................... 424/448, 449; 514/946

[56] References Cited

U.S. PATENT DOCUMENTS 4,081,537  3/1978  Hofmeister et al. .................... 424/238
5,376,377  12/1994  Gale ........................................ 424/448

FOREIGN PATENT DOCUMENTS 2001618  10/1989  Canada .

OTHER PUBLICATIONS

Nelder et al., "Selection and Use of Crystallization Inhibitors . . . ", *The Computer Journal*, 7 (1965), S. 308–313.

Lipp et al., "Rational Design of Prodrugs . . . ", *Proceed. Intern. Symp. Control. Rel. Bioact. Mater.*, 22 (1995), Controlled Release Society, Inc.

R. Lipp, "X–Ray Structure Determination of Crystals . . . ", *Pharmaceutical Research*, Oct. 1994 (Supplement), vol. 11, No. 10, S–213.

R. Guy et al., "Percutaneous Penetration Enhancement . . . ", *Library of Congress Cataloging-in-Publication Data*, 1992.

*Primary Examiner*—Thurman K. Page
*Assistant Examiner*—Sharon Howard

[57] ABSTRACT

An agent for transdermal administration is described, which is characterized in that it contains gestodene esters with 1 to 20 carbon atoms in the ester radical optionally in combination with one or two estrogen(s).

15 Claims, 2 Drawing Sheets

AGENT FOR TRANSDERMAL ADMINISTRATION THAT CONTAINS GESTODENE ESTERS

The invention relates to an agent for transdermal administration, characterized in that it contains gestodene esters with 1 to 20 carbon atoms in the ester radical optionally in combination with one or more estrogen(s).

These gestodene esters are characterized by the general formula

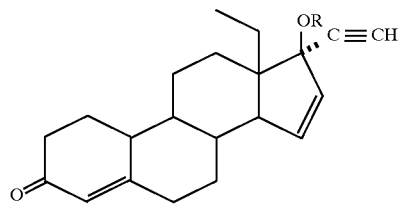

in which R means an acyl radical with 1 to 20 carbon atoms.

The invention preferably relates to agents for transdermal administration with gestodene esters with 2 to 12 carbon atoms in the acyl radical and especially agents which contain gestodene alkanoates with 2 to 8 carbon atoms in the alkanoyl radical. As suitable gestodene esters that were unknown up until now, gestodene propionate, gestodene valerate, and especially gestodene capronate can be especially emphasized, which also are object of this invention, and their production is described at a later point.

As is generally known, gestodene itself is a substance with unusually high gestagenic effectiveness (B. Düsterberg, Steroids 43, 1984, 43 ff), which is used in combination with estrogenically effective substances for the production of contraceptive agents (Femovan®) that are to be administered orally. It is known that gestodene itself can be administered transdermally (EP-A 0370220). Further, it is known that the esters of gestodene also exert a strong gestagenic action in the case of oral administration (U.S. Pat. No. 4,081,537).

It has now been found, surprisingly enough, that gestodene esters can be used optionally in combination with one or more estrogens often better for the production of an agent for transdermal administration of active ingredients than combination preparations that contain gestodene itself.

By the esterification of the 17β-position hydroxyl group of the gestodene, the physicochemical properties of this substance are targeted and bioreversibly altered toward pro-drug formation.

If the skin penetration of gestodene is compared with that of its esters, the latter are generally distinguished by considerably higher transdermal flows. This is especially true in the processing of esters in matrix-transdermal systems, such as, for example, those of the acrylate type (as are described at a later point in Example 2).

The unusually high transdermal flows are due especially to the surprisingly advantageous solubilities that have been found for the above-mentioned esters of the gestodene in conventional skin contact adhesives and mixtures of them with cosolvents of respective penetration enhancers. Based on these properties, highly loaded and stable matrix transdermal systems with molecularly dispersely distributed gestodene-pro-drugs can now be produced for the first time. Even active ingredient loads that on a molecular basis are higher by a factor of 10 than the comparable ones achievable for gestodene result in stable systems. This is a decisive advantage compared to the gestodene-containing systems, which are previously known from EP-A 0370220, since the difference in concentration between transdermal systems and skin is decisively responsible for the levels of the transdermal flows that can be achieved.

Thus, with the aid of the agent according to the invention, it is possible to achieve high uniform flows of gestodene esters with comparatively small transdermal systems.

It was already mentioned that in addition to gestodene esters, the agent according to the invention can also contain one or more estrogens. Suitable estrogens are, for example, estradiol, estriol, ethinylestradiol, mestranol, 14α,17α-ethanoestra-1,3,5(10)-triene-3,17β-diol (WO 88/01275), the 14α,17α-ethanoestra-1,3,5(10)-triene-3,16α,17β-triol (WO 91/08219) and their esters (EP-A 163596), such as estradiol dipropionate, estradiol dihexanoate and estradiol didecanoate. In addition to 1 or 2 gestodene esters, these combination preparations according to the invention contain preferably 1 to 3, and especially 1 to 2 estrogen(s).

For the production of pharmaceutical preparations, the active ingredient or the active ingredient mixture can be dissolved or suspended in suitable volatile solvents and/or penetration-enhancing agents. The solutions or suspensions that are obtained can be mixed with conventional adjuvants, such as matrix formers and bactericides, and after sterilization are optionally decanted in conventional metering tanks. In contrast, it is also possible, however, to further process these solutions or suspensions with emulsifiers and water to produce lotions or ointments. Sprays—optionally by the addition of a propellant—that can be decanted in the conventional metering tanks can also be produced.

Suitable volatile solvents are, for example, lower alcohols, ketones or lower carboxylic acid esters, such as ethanol, isopropanol, acetone or ethyl acetate, polar ethers, such as tetrahydrofuran, lower hydrocarbons, such as n-hexane, cyclohexane or gasoline or else halogenated hydrocarbons, such as dichloromethane, trichloromethane, trichlorotrifluoroethane and trichlorofluoromethane. It goes without saying that mixtures of these solvents are also suitable.

Suitable penetration-enhancing agents are, for example, monovalent or multivalent alcohols, such as ethanol, 1,2-propanediol or benzyl alcohol, saturated and unsaturated fatty alcohols with 8 to 18 carbon atoms, such as lauryl alcohol or cetyl alcohol, hydrocarbons, such as mineral oil, saturated and unsaturated fatty acids with 8 to 18 carbon atoms, such as stearic acid or oleic acid, fatty acid esters with up to 24 carbon atoms or dicarboxylic acid diesters with up to 24 carbon atoms.

Fatty acid esters that are suitable as penetration-enhancing agents are, for example, those of acetic acid, hexanoic acid, lauric acid, myristic acid, stearic acid, palmitic acid or oleic acid, such as, for example, methyl esters, ethyl esters, propyl esters, isopropyl esters, butyl esters, sec-butyl esters, isobutyl esters, tert-butyl esters or monoglycerol esters of these acids. Especially preferred esters are those of myristic acid or oleic acid, such as their methyl esters, their isopropyl esters or their monoglycerol esters. Suitable dicarboxylic acid diesters are, for example, diisopropyl adipate, diisobutyl adipate and diisopropyl sebacate.

Other penetration-enhancing agents are phosphatide derivatives, such as lecithin, terpenes, amides, ketones, urea and its derivatives or ethers, such as, for example, diethylene glycol monoethyl ether or dimethyl isosorbide. It also goes without saying that mixtures of these penetration-enhancing agents are also suitable for the production of the agent according to the invention.

The concentration at which the active ingredient or the active ingredient mixture is optimally dissolved or suspended in the solvent is usually 0.01 to 40% by weight for gestodene esters. In the case of estrogens, the concentration depends, of course, on the type of active ingredient used and the individual dose desired; it must be determined in individual cases by means of preliminary tests that are familiar to one skilled in the art, such as, for example, the determination of achievable active-ingredient concentrations in plasma, after dermal administration of selected systems according to the invention. In general, active ingredient concentrations of 0.01 to 25% by weight of estrogen on average according to the invention will also be sufficient. The ratio by weight of gestodene ester(s) to estrogen(s) is approximately 5:1 to 1:10 in the case of the combination preparations.

The therapeutically necessary transdermal daily dose is indication-dependent and lies in the range of about 25–75 $\mu$g of gestodene per day. The gestodene esters are dosed in equimolar portions to take into consideration the increase in molecular weight by prodrug formation. For example, the daily dose for gestodene caproate is about 30–100 $\mu$g. For a transdermal system with a surface area of 20 cm$^2$, this means that transdermal flows of up to 0.2 $\mu$g of gestodene capronate/cm$^2$/h are necessary. In in vitro studies with suitable formulations, it was shown that the latter are considerably exceeded.

Very uniform administration with a set dosage of the active ingredient or active ingredient mixture can be achieved if the active ingredient or the mixture is packed in a transdermal therapeutic system (TTS). Suitable transdermal therapeutic systems are those that are used conventionally for percutaneous administration of active ingredients (Yie W. Chien: "Transdermal Controlled Systemic Medications," Marcel Dekker, Inc., New York and Basel 1987, Dr. Richard Baker: "Analysis of Transdermal Drug Delivery Patents 1934 to 1984" and "Analysis of Recent Transdermal Delivery Patents, 1984–1986 and Enhancers" Membrane Technology & Research 1030 Hamilton Court Menlo Park Calif. 94025 (415) 328-2228).

Thus, for example, a transdermal therapeutic system can be used that consists of a) an impermeable cover layer, one to three matrix layer(s) adhering to the cover layer, that contains the gestodene ester or esters, optionally estrogen(s) and optionally penetration-enhancing agents, permeably self-adhering for these components or covered or surrounded by a skin contact adhesive that optionally contains penetration-enhancing agents, a removable protective layer, or b) a cover provided with a contact adhesive that optionally contains penetration-enhancing agents, one to three (in each case) matrix layer(s) that leave uncovered a contact adhesive border, fastened by means of a cover to the contact adhesive, that contains the gestodene ester or esters, optionally the estrogen(s) and penetration-enhancing agents, and a removable protective layer, or c) an impermeable cover layer, one to three pharmaceutical agent reservoir(s) that are present on or in the cover layer, that contain the gestodene ester or esters, optionally the estrogen(s) and optionally penetration-enhancing agents, one to three polymer layer(s) that are permeable to these components, a permeable skin contact adhesive layer that optionally contains penetration-enhancing agents, and a removable protective layer.

A transdermal therapeutic system according to variant a) represents a simple matrix system. It can be, for example, round, oval or rectangular in shape and be produced as follows.

A solution or suspension of up to 40% by weight of active ingredient or active ingredient mixture, 0–40% by weight of a penetration-enhancing agent, 30–70% by weight of a medicinally usual adhesive, supplemented with a suitable volatile solvent to make 100% by weight, is painted on a flat, impermeable cover layer. After drying, a second and optionally later even a third layer that optionally contains an active ingredient, penetration-enhancing agents and an adhesive can be applied to this layer and dried. Then, the matrix system is provided with a removable protective layer.

If a medicinally usual matrix former which, after the system dries, does not adhere to the skin or does so inadequately is used, the system can be covered or surrounded in addition with a skin contact adhesive before the application of the removable protective layer.

Suitable solvents and penetration-enhancing agents are, for example, the already mentioned liquids of this type. As medicinally usual adhesives, for example, polyacrylates, silicones, polyurethanes, block polymers, styrene-butadiene copolymers as well as natural or synthetic rubbers, such as, for example, polyisobutylenes, are suitable. As additional matrix formers, cellulose ethers, polyvinyl compounds or silicates are suitable. To increase adhesiveness, the usual additives, such as, for example, adhesion-making resins and oils, can be added to the obtained matrix.

As a protective layer, all films that are usually used in the case of transdermal therapeutic systems are suitable. Such films are, for example, siliconized or fluoropolymer-coated.

As a cover layer, for example, 10 to 100 $\mu$m thick films made of polyethylene or polyester can be used selectively pigmented or metallized in this system. The pharmaceutical agent layer that is applied thereupon preferably has a thickness of 20 to 500 $\mu$m. The dispensing of active ingredients preferably is done over a surface area of 5 to 100 cm$^2$.

In the case of multilayer matrix systems, the gestodene ester or esters and optionally the penetration enhancers can be introduced into, e.g., the matrix applied to the impermeable cover layer, while the layer or layers that are present below contains the estrogens and optionally also penetration enhancers. In contrast, it is also possible, however, to place several active ingredient-containing matrices beside one another in such a transdermal system.

According to variant b, a transdermal therapeutic matrix system can also be, for example, round, oval or rectangular and can be produced as follows.

A cover is coated with a skin contact adhesive. Then, one to three punched-out areas of a matrix layer that is provided with an impermeable cover, that contains the gestodene ester or esters, optionally the estrogen(s) and penetration-enhancing agents are attached to the latter via TTS so that the cover has a sufficient edge to attach to the skin and, in the case of multiple areas, also sufficient interspaces, and provides it with a removable protective layer. The materials used in this matrix system can be the same as those of variant a.

A transdermal, therapeutic reservoir system according to variant c can also be, for example, round, oval or rectangular and can be represented as follows;

An impermeable film is worked by heat and/or suction in such a way that one to three blisters holding 0.1 to 3 ml result. The latter are filled with an active ingredient-containing solution or suspension that contains 1–50% by weight of active ingredient or active ingredient mixture with a penetration-enhancing agent. The active ingredient-containing solution or suspension can also be thickened with up to 10% by weight of matrix former.

As a cover for the reservoir to the skin, a welded or glued permeable polymer layer, to which a permeable skin contact adhesive layer and a removable protective layer are attached, is used.

In this system, the above-mentioned penetration-enhancing agents can be used. As a permeable polymer layer, for example, a 20 to 200 μm thick film made of cellulose esters, cellulose ethers, silicones or polyolefin compounds is used. By altering this polymer layer, the rate of diffusion of the active ingredient or active ingredient mixture can be varied within wide limits.

For an adhesive and protective layer, the same materials that are described in the transdermal therapeutic system according to variant a are suitable.

In the case of the production of transdermal therapeutic systems with two or three active ingredient-containing matrix layers or pharmaceutical agent reservoirs that are arranged beside one another, it is often suitable to introduce the gestodene ester or esters into one and the estrogen or estrogens into the other. In such cases, the active ingredient-containing matrix systems or pharmaceutical agent reservoirs can contain not only differing active ingredients, but also differing penetration-enhancing agents.

In the case of the matrix systems according to variants a or b, care must be taken to leave sufficient distance between the areas to prevent diffusion of active ingredients into the respective other areas. In the case of the reservoir systems according to variant c, it is possible to provide the individual reservoirs with differing permeable polymer layers to adapt the diffusion flow of the individual active ingredients to the respective needs.

BRIEF DESCRIPTION OF THE DRAWINGS

Other features of the transdermal systems according to the invention can be explained based on the attached drawings, which are not true-to-scale.

Figure 1:
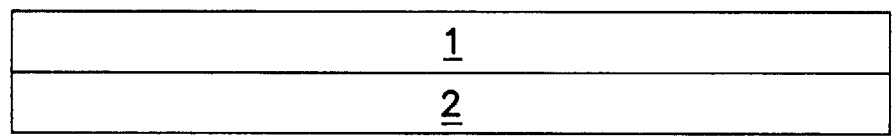
FIG. 1 shows a cross section through a simple round matrix system according to variant a without the removable protective layer. It consists of impermeable cover layer 1 and pharmaceutical agent-containing matrix layer 2.

In addition to transdermal therapeutic systems, also other galenical preparations are suitable for transdermal administration of gestodene esters.

An emulsion gel for transdermal administration consists of, for example, the active ingredient or active ingredient mixture, penetration-enhancing agents, emulsifiers (and ambiphilic representatives of penetration-enhancing agents can be used as emulsifiers) and optionally matrix formers. A typical formulation consists of 0.1–25% by weight of active ingredient or active ingredient mixture, 0–10% by weight of emulsifier, 0–5% by weight of matrix former, 0 to 50% by weight of penetration-enhancing agents and water to make 100% by weight. The agent is emulsified in the conventional way and mixed, if necessary, with the conventional antioxidants, preservatives, etc.

One-phase gels are obtained, for example, by detaching or suspending the active ingredient or the active ingredient mixture in solvents such as water, lower alcohols or their mixtures, optionally with the addition of penetration-enhancing agents and thickening with matrix formers.

Typical formulations for such gels contain 0.01–25% by weight of active ingredient or active ingredient mixture, 1–20% by weight of matrix former, 0 to 40% by weight of penetration-enhancing agents are supplemented with the solvent to make 100% by weight.

Also, these gels can optionally contain antioxidants, preservatives, etc.

A typical spray formulation is, for example, the following:

1–25% by weight of active ingredient or active ingredient mixture, 0–20% by weight of matrix former, 0–60% by weight of penetration-enhancing agent supplemented with solvents and optionally propellants to make 100%. If pressurized-gas packings are used, the propellant can be omitted.

The gestodene ester-containing agents for transdermal administration according to the invention can be used for treatment of the same diseases as the previously known agents, for example, ones to be administered orally that contain highly effective gestagens. Moreover, the optionally estrogen-containing preparations according to the invention can also be used for contraception. The agents according to the invention have special advantages in treating diseases that require long-term treatment with relatively high dosages of active ingredients. Here, the frequency of administration can be significantly reduced and a significantly more uniform blood plasma level can be achieved. It is also advantageous that no gastrointestinal side-effects are to be expected and in the case of estrogen-containing combination preparations, the first liver passage is avoided and the estrogen dose can be reduced.

These advantages make the estrogen-free monotherapeutic agents of this invention appear especially suitable for treating, for example, endometriosis, gestagen-dependent tumors, benign breast diseases or premenstrual syndrome.

The transdermal use of estrogens in sequential or continuous combination with gestodene esters offers special advantages, for example, for treating menopausal symptoms, for the prevention of osteoporosis, for cycle regulation and for cycle stabilization.

The embodiments below are used for a more detailed explanation of the invention. The following commercial products are used in them:

Polyester film of 0.074 mm thickness (Skotchpak® 1009 of the 3M manufacturer; polypropylene film (Celgard® 2500) of the Celanese manufacturer, Linerfolie Skotchpak [liner film scotchpak]® 1022 and 1360 of the 3M manufacturer; Transferkleber [transfer adhesive] 9871 of the 3M manufacturer, polyacrylester adhesive of Sichello type® J 6610-21 of the Henkel KG manufacturer, polyisobutylene adhesive of Oppanol® B 15SF type of the BASF manufacturer, polyacrylate ester adhesive of the Gelva® Monsanto type, silicone adhesive of X-7-4502 type of the Dow Corning manufacturer and hydroxypropyl cellulose of the Klucel® HXF type of the Hercules manufacturer.

A: AGENT FOR TRANSDERMAL ADMINISTRATION

Example 1

In 62.4 g of a 50% solution of silicone adhesive in gasoline, 0.8 g of gestodene capronate 8.0 g of 1,2-propanediol are introduced in succession while being stirred. After the batch is degassed, the mixture is introduced onto polyester film by means of a coating device, so that after the volatile solvent is removed, a uniform film of 40 g/m$^2$ of solid deposit results. Then, it is laminated with a fluoropolymer-coated polyester liner. The laminate thus obtained is divided into round individual patches with a surface area of 10 cm$^2$ by means of a punching device and packaged in aluminum foil. FIG. 1 shows a cross section through this patch without a polyester liner. After the liner-foil is removed, the patch adheres to the skin.

The determination of content yields a uniform active ingredient distribution of 0.08 mg/cm$^2$ on average.

Example 2

10 g of gestodene capronate is introduced into 80 g of a 50% solution of polyacrylic acid ester in ethyl acetate (g:g) while being stirred and is worked up as described in Example 1.

The determination of content yields a uniform active ingredient distribution of 8 mg/cm$^2$ on average.

Example 3

In 170 g of a 50% solution of polyisobutylene adhesive in acetone/gasoline, 5.0 g of gestodene valerate 10.0 g of isopropyl myristate are dissolved in succession while being stirred. After the batch is degassed, the solution is introduced onto polyester film by means of a coating device, so that after the volatile solvent is removed, a uniform film of 100 g/m$^2$ of solid deposit results. Then, it is laminated with a siliconized active ingredient-free liner foil. The laminate thus obtained is divided into individual patches with a surface area of 10 cm$^2$ by means of a punching device and packaged in aluminum foil. After the liner-foil is removed, the patch adheres to the skin.

The content of gestodene valerate is 0.5 mg/cm$^2$ on average.

Example 4

In 112 g of a 50% solution of polyacrylester adhesive in acetone/gasoline, 3.5 g of estradiol 3.5 g of gestodene capronate and 7.0 g of 1,2-propanediol with 10% 1-dodecanol are dissolved or suspended in succession while being stirred. After the batch is degassed, the mixture is introduced onto polyester film by means of a coating device, so that after the volatile solvent is removed, a uniform film of 70 g/m$^2$ of solid deposit results. Then, it is laminated with a siliconized active ingredient-free liner-foil. The laminate thus obtained is divided into individual patches of a 5 cm$^2$ surface area by means of a punching device and packaged in aluminum foil. After the liner-foil is removed, the patch adheres to the skin.

In a like manner, the content of estradiol and gestodene capronate is approximately 0.35 mg/cm$^2$ each.

Example 5

Figure 2:
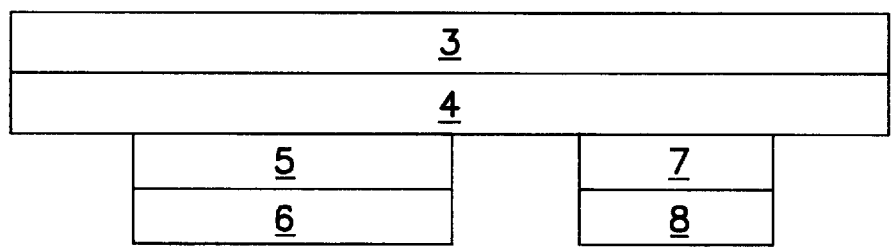
FIG. 2 shows a cross section through a matrix system according to variant b without the removable protective layer.
Figure 3:
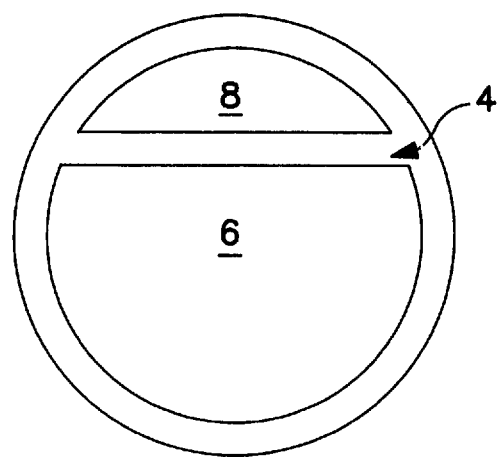
FIG. 3 shows the top view of this system. The system consists of cover 3, which is provided with a contact adhesive layer 4. Two pharmaceutical agent-containing matrix layers 6 and 8 are fastened to this contact adhesive layer by means of impermeable covers 5 and 7.

Analogously to Example 1, two different segment-like matrix systems are produced that have the design depicted in FIGS. 2 and 3. Matrix system I consists of matrix 8, provided with a polyester film 7, of the following composition 1.0 mg of gestodene acetate 5.0 mg of isopropyl myristate and 44 mg of acrylate adhesive and has a surface area of 5 cm$^2$.

Matrix system II consists of matrix layer 6, provided with a polyester film 5, of the following composition 2.0 mg of estradiol 10.0 mg of isopropyl myristate and 88 mg of acrylate adhesive and has a surface area of 10 cm$^2$.

Both matrix systems are stuck onto a cover film that is coated with a skin contact adhesive, as FIG. 3 shows. After lamination and punching out, patches of the type shown in FIGS. 2 and 3 result.

Example 6

A polyester film of a 7.4 cm diameter is worked by suction and heat, so that a round blister with a surface area of 10 cm$^2$ results. The latter is filled with 1 ml of a suspension of 2.5 mg of ethinyl-estradiol and 2.5 mg of gestodene valerate in 1,2-propanediol, which contains 10% lauric acid. A polypropylene or cellulose acetate butyrate film is welded on the edge. Depending on the pressure per unit of time, the sealing temperature is between 70° C. and 100° C. Skin-adhesive film is transferred to the permeable polymer layer. The patch is provided with a liner and packaged in aluminum foil.

Figure 4:
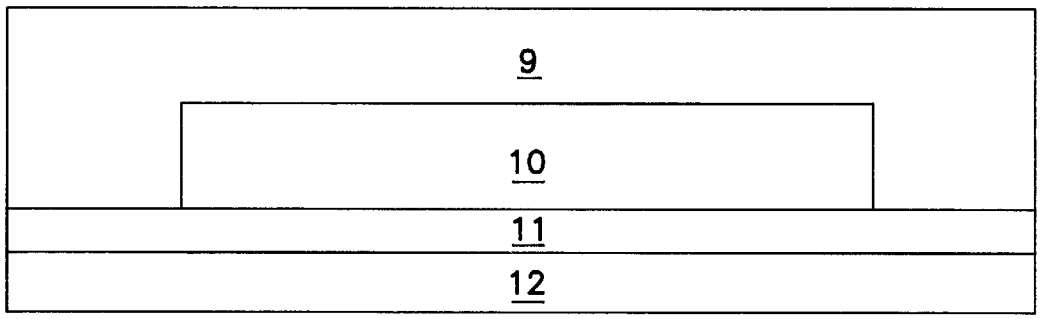
FIG. 4 shows a cross section through a round, one-chamber reservoir system according to variant c, without the removable protective layer. It consists of impermeable cover layer 9, pharmaceutical agent reservoir 10, permeable polymer layer 11 and skin contact adhesive 12.

FIG. 4 shows a cross section through a patch of this type without a liner.

Example 7

Analogously to Example 6, a polyester film is worked so that two semicircular blisters with a surface area of 7.5 cm$^2$ each that are separated from one another by a ridge result.

Reservoir I is filled with 0.75 ml of a suspension of 1.5 mg of gestodene acetate in 1,2-propanediol and reservoir II is filled with 0.75 ml of such a one of 3.0 mg of estradiol in 1,2-propanediol.

Figure 5:
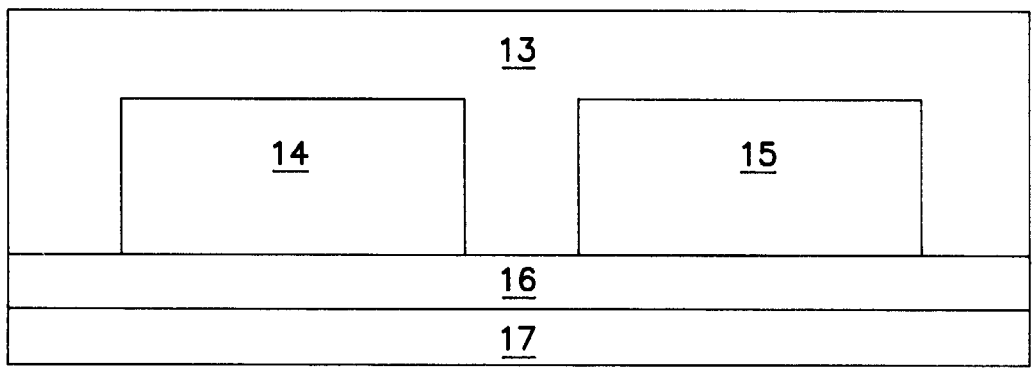
FIG. 5 shows a cross section through a round, two-chamber reservoir system according to variant c without the removable protective layer. It consists of impermeable cover layer 13, two semi-circular pharmaceutical agent reservoirs 14 and 15, permeable polymer layer 16 and skin contact adhesive layer 17.

The further completion of the patch is carried out as described in Example 5. FIG. 5 shows a cross section through such a patch without a liner.

Example 8

In 76.78 g of ethanol (96% by vol.) or isopropanol, 0.2 g of estradiol 0.02 g of gestodene propionate 10.0 g of 1,2-propanediol and 10.0 g of isopropyl myristate are dissolved in succession. Then, 3 g of hydroxypropyl cellulose is added to the solution, and air is removed from it. After 2 hours of steeping time, the gel is filled in aluminum tubes with three-fold inner protective varnishing.

The determination of content yields a homogeneous active ingredient distribution in gel with values of 95% at 105% of the setpoint value.

Example 9

20.00 g of gestodene capronate is dissolved in 1000 g of isopropyl myristate, sterilized by filtration and decanted in 5 ml medicine bottles under aseptic conditions.

B: SYNTHESES

Example 1

A solution of 25 g of gestodene in 150 ml of pyridine is mixed with 75 ml of propionic anhydride, after addition of 2.5 g of 4-pyrrolidinopyridine, it is held at room temperature for 16 hours and then heated for 3 hours to 60° C. The reaction product is precipitated with 3 l of ice water, and the precipitate is filtered out, washed and taken up in dichloromethane. The organic phase is dried and concentrated by evaporation in a vacuum. The residue of 29.6 g is treated with activated carbon and recrystallized from dichloromethane/diisopropyl ether. 24.2 g of gestodene propionate with a melting point of 171.9° C. is obtained. $[\alpha]_D = -117°$ (chloroform). $UV_{\leq 238} = 18500$ (methanol).

Example 2

A solution of 10 g of gestodene in 60 ml of pyridine is mixed with 30 ml of valeric anhydride and after the addition of 1.0 g of 4-pyrrolidinopyridine, it is held at 60° C. for 20 hours. The reaction solution is stirred into 500 ml of water, the mixture is stirred for 5 hours, and the precipitate that is produced is washed with water and dried. The crude product thus obtained is chromatographed with a pentane-diethyl ether gradient (0–50% diethyl ether) on silica gel (diameter of the column 6 cm, filling height 30 cm, grain size 0.015–0.04 mm). 11.8 g, which yields 7.9 g of gestodene valerate that is recrystallized from diethyl ether-diisopropyl ether, is eluted.

Melting point 114.4° C. $[\alpha]^D = -102°$ (chloroform). $UV_{\leq 238} = 18900$ (methanol).

Example 3

A solution of 15 g of gestodene in 90 ml of pyridine is mixed with 45 ml of decanoic anhydride and, after the addition of 1.5 g of 4-pyrrolidinopyridine, it is held at 60° C. for 20 hours. The reaction solution is stirred into 1 l of water and the mixture is then subjected to steam distillation for 3 hours. The oily product that is produced is taken up in dichloromethane, and the solution is washed with water, dried with sodium sulfate and concentrated by evaporation in a vacuum. The residue of 19.5 g is chromatographed with a hexane-ethyl acetate gradient (0–30% ethyl acetate) on silica gel (diameter of the column 8 cm, filling height 35 cm, grain size 0.015–0.04 mm). 11.9 g of gestodene capronate is eluted as oil. $[\alpha]_D = -101°$ (chloroform) $UV_{\leq 238} = 18200$ (methanol).

We claim:

1. A transdermal therapeutic system (TTS), comprising one to three gestodene ester compounds with 1 to 20 carbon atoms in the ester radical, optionally in combination with a gestodene compound and/or with one to three estrogen compound(s), and further comprising:
   a)
      (i) an impermeable cover layer,
      (ii) one to three acrylate matrix layer(s) adhering to said cover layer and comprising said compounds and, optionally, penetration-enhancing agents, wherein said matrix layer(s) are permeable to said compounds and optional penetration-enhancing agents and are self-adhering to skin, or wherein said matrix layer(s) are covered or surrounded by a skin contact adhesive that optionally contains penetration-enhancing agents, and
      (iii) a removable protective layer which covers said matrix layer, or
   b)
      (i) a cover provided with a contact adhesive that optionally contains penetration-enhancing agents,
      (ii) one to three acrylate matrix layer(s), each of which is attached to an impermeable cover, which in turn is attached to said contact adhesive, leaving uncovered a contact adhesive border, wherein said matrix layer(s) contain said compounds and, optionally, penetration-enhancing agents, and
      (iii) a removable protective layer which covers said matrix layer, or
   c)
      (i) an impermeable cover layer,
      (ii) one to three pharmaceutical agent reservoir(s) that are present on or in the cover layer and that contain said compounds and, optionally, penetration-enhancing agents,
      (iii) one to three acrylate polymer layer(s) that are in contact with and are permeable to said compounds and penetration-enhancing agents,
      (iv) a permeable skin contact adhesive layer that is in contact with the polymer layer(s) and optionally contains penetration-enhancing agents, and
      (v) a removable protective layer which covers said polymer layer.

2. A TTS according to claim 1, wherein said gestodene esters have 2 to 12 carbon atoms in the ester radical.

3. A TTS according to claim 1, wherein said gestodene esters are alkanoates with 2 to 8 carbon atoms in the alkanoyl radical.

4. A TTS according to claim 1, wherein said estrogens are estradiol, estriol, 17α-ethinylestradiol, mestranol, 14α,17α-ethanoestra-1,3,5(10)-triene-3,17β-diol, 14α,17α-ethanoestra-1,3,5(10)-triene-3,16α,17β-triol, or esters of these compounds.

5. A TTS according to claim 1, further comprising an active ingredient-containing matrix layer or a pharmaceutical agent reservoir.

6. A TTS according to claim 1, which contains two or three active ingredient-containing matrix layers or pharmaceutical agent reservoirs.

7. A TTS according to claim 6, wherein the active ingredient-containing matrix layers or the pharmaceutical agent reservoirs contain different active ingredients.

8. A method for the transdermal administration of an active ingredient or active ingredient mixture, comprising placing on the skin of a subject a TTS of claim 1.

9. The method of claim 8, wherein the estrogen(s) are estradiol, estriol, 17α-ethinylestradiol, mestranol, 14α,17α-ethanoestra-1,3,5(10)-triene-3,17β-diol, 14α,17α-ethanoestra-1,3,5(10)-triene-3,16α-17β-triol or esters of these estrogens.

10. A method for transdermal contraception, for the treatment of endometriosis, for the treatment of gestagen-dependent tumors or for the treatment of premenstrual syndrome, comprising placing on the skin of a subject a TTS which comprises one to three acrylate matrix layers and one to three gestodene esters with 1 to 20 carbon atoms in the ester radical, optionally in combination with gestodene, but which does not contain estrogen.

11. A method for the treatment of menopausal symptoms, for the prevention of osteoporosis, for cycle regulation, for cycle stabilization or for transdermal contraception, comprising placing on the skin of a subject a TTS of claim 1.

12. A TTS of claim 3, wherein said gestodene alkanoates have 3, 5 or 6 carbon atoms in the alkanoyl radical.

13. A TTS of claim 12, wherein said gestodene alkanoate is gestodene propionate.

14. A TTS of claim 12, wherein said gestodene alkanoate is gestodene valerate.

15. A TTS of claim 12, wherein said gestodene alkanoate is gestodene capronate.

* * * * *